(12) United States Patent
Shiozawa et al.

(10) Patent No.: US 6,660,847 B1
(45) Date of Patent: Dec. 9, 2003

(54) RHEUMATOID ARTHRITIS GENE

(75) Inventors: Shunichi Shiozawa, 11-6, Takeno-dai 2-chome, Nishi-ku, Kobe-shi, Hyogo (JP); Koichiro Komai, Hyogo (JP)

(73) Assignee: Shunichi Shiozawa, Hyogo (JP)

( * ) Notice: Subject to any disclaimer, the term of this patent is extended or adjusted under 35 U.S.C. 154(b) by 0 days.

(21) Appl. No.: 09/936,989

(22) PCT Filed: Mar. 21, 2000

(86) PCT No.: PCT/JP00/01697

§ 371 (c)(1),
(2), (4) Date: Oct. 30, 2001

(87) PCT Pub. No.: WO00/56888

PCT Pub. Date: Sep. 28, 2000

(30) Foreign Application Priority Data

Mar. 20, 1999 (JP) ............................................ 11-116933

(51) Int. Cl.[7] ........................ C07H 21/02; C07H 21/04
(52) U.S. Cl. ................... 536/23.5; 536/23.1; 536/24.31; 536/24.33
(58) Field of Search ............................... 536/23.1, 23.5, 536/24.31, 24.33

(56) References Cited

U.S. PATENT DOCUMENTS 5,612,212 A * 3/1997 Gewirtz ................... 435/172.3

OTHER PUBLICATIONS

Komai et al., Arthritis and Rheumatism, Sep. 1999, 4219 Suppl., ppS392, Abstract 1926.*

* cited by examiner

*Primary Examiner*—Carla J. Myers
(74) *Attorney, Agent, or Firm*—Wenderoth, Lind & Ponack, L.L.P.

(57) ABSTRACT

As a disease gene for rheumatoid arthritis present in human chromosome X and a method of diagnosing rheumatoid arthritis, a disease gene, which is a mutant of protooncogene Dbl transcribing an mRNA that encodes the cDNA of which the sequence from the 2679th to 2952nd bases is shown in SEQ ID NO: 1, which disease gene transcribes an mRNA encoding the cDNA of which the region from the 20th to 274th bases in SEQ ID NO: 1 is substituted with the sequence of SEQ ID NO: 2, and a method for diagnosing rheumatoid arthritis by detecting the mRNA of the above-described gene or its expression product in a biological specimen, is provided.

5 Claims, 1 Drawing Sheet

Figure 1

```
         2680       2690       2700       2710       2720       2730
Normal; tcttcagcagaatgatgaaaagcaacaggagctttataagtactgaggaaactgaattg
RA    ; tcttcagcagaatgaagaacctgtgtcggagatggctctcctatattgatgaagctact
         L  Q  Q  N  D  E  K  Q  Q  G  A  F  I  S  T  E  E  T  E  L
         L  Q  Q  N  D  E  D  L  C  R  R  W  L  S  Y  I  D  E  A  T 2740       2750       2760       2770       2780       2790
        gaacacaccagcactgtggtggaggtctgtgaggcaattgcgtcagttcaggcagaagca
        atgtcaaatggcaagtag
         E  H  T  S  T  V  V  E  V  C  E  A  I  A  S  V  Q  A  E  A
         M  S  N  G  K  *

2800       2810       2820       2830       2840       2850       2860
        aatacagtttggactgaggcatcacaatctgtagaaatctctgaagaacctgcggaatggt
         N  T  V  W  T  E  A  S  Q  S  V  E  I  S  E  E  P  A  E  W 2870       2880       2890       2900       2910
        caagcaactatttctaccccacttatgatgaaaatgaagaagaaaataggcccctcatg
         S  S  N  Y  F  Y  P  T  Y  D  E  N  E  E  E  N  R  P  L  M 2920       2930       2940       2950
        agacctgtgtcggagatggctctcctatattga
         R  P  V  S  E  M  A  L  L  Y  *
```

RHEUMATOID ARTHRITIS GENE

This application is a 371 of PCT/JP00/01697 filed Mar. 21, 2000.

BACKGROUND OF THE INVENTION

1. Field of the Invention

The present invention relates to the disease gene of rheumatoid arthritis present in the human X chromosome and a method for diagnosing rheumatoid arthritis by detecting the presence of the disease gene or its expression product.

2. Description of Related Art

Although aspects, particularly the pathological process, of arthritis and arthritis mutilans which cause rheumatoid arthritis, have been clarified through various investigations, because most autoimmune diseases associated with rheumatoid arthritis developed or worsen into the disease only when various causative factors coincide, the interaction itself of multiple factors must be clarified to understand the disease and to develop appropriate methods of treatment.

The number of patients with rheumatoid arthritis in the world is 1% or less (N. Engl. J. Med. 322: 1277–1289, 1990), but among siblings of patients, over 8% develop the disease (Cell. 85: 311–318, 1996), which leads to the notion that some genetic factor may be involved. However, molecular genetic procedures and genetic engineering processes used conventionally to discover the genetic factor of diseases may not be effective for autoimmune diseases. Such problem is caused by the fact that autoimmune diseases do not develop through mechanisms as simple as those of cancer, wherein abnormal growth of one mutated gene occurs. Further, although classical genetic procedures which search for genetic basis of a disease revealed that autoimmune diseases are caused by multiple genetic factors, it has not been successful in discovering its entrails or its body. Thus, almost nothing about the entity, or even the locus, of genes associated with rheumatoid arthritis has been known.

By performing linkage analysis using microsatellite markers on rheumatoid arthritis patients and their relatives, the present inventors identified three loci of rheumatoid arthritis genes (International Immunology 10(12): 1891–1895, 1998; Journal of Clinical Rheumatology 4(3): 156–158, 1998) and filed a patent application for the following disease genes (PCT/JP98/01665).

(1) A disease gene of rheumatoid arthritis located within ±1 centi Morgan vicinity of a DNA sequence on human chromosome 1 to which microsatellite marker(s) D1S214 and/or D1S253 hybridize(s)

(2) A disease gene of rheumatoid arthritis located within ±1 centi Morgan vicinity of a DNA sequence on human chromosome 8 to which microsatellite marker D8S556 hybridizes.

(3) A disease gene of rheumatoid arthritis located within ±1 centi Morgan vicinity of a DNA sequence on human chromosome X to which microsatellite marker(s) DXS1001, DXS1047, DXS1205, DXS1227 and/or DXS1232 hybridize(s).

The present inventors identified, as a result of further studies on each of the rheumatoid arthritis genes specified in the above-described previous application, the specific gene regarding the disease gene (3) described above and determined its molecular structure.

SUMMARY OF THE INVENTION

In order to solve the above-described problems, the present invention provides a cDNA of a disease gene for rheumatoid arthritis, which has the base sequence of SEQ ID NO: 1.

The present invention also provides a DNA fragment, which is a part of such cDNA and necessarily contains the base sequence from 2693rd to 2702nd of SEQ ID NO: 1, a protein expressed by the above disease gene, a peptide which is a part of such protein, and an antibody against such protein.

Further, the present invention provides a method for diagnosing rheumatoid arthritis comprising the detection of the mRNA from the above disease gene or the above protein in a biological specimen.

The present invention further provides a method for the functionally complementing Dbl deficiency.

BRIEF DESCRIPTION OF THE DRAWING

FIG. 1 shows the base sequence of the 2679th to 2952nd bases of the Dbl gene cDNA in its normal form (see bases 2679 to 2952 of SEQ ID NO: 5), the corresponding base sequence of the cDNA of the disease gene of RA (see bases 2679 to 2757 of SEQ ID NO: 1), and the respective amino acid sequences (1 letter notation) encoded by these sequences (see amino acid residues 836 to 860 of SEQ ID NO: 2 and amino acid residues 836 to 925 of SEQ ID NO: 6).

DESCRIPTION OF THE PREFERRED EMBODIMENTS

Hereinafter, embodiments of the present invention having the above-described characteristics will be described.

The cDNA of the disease gene for rheumatoid arthritis of the present invention (hereinafter referred to as "cDNA") is a variant sequence of known protooncogene Dbl cDNA (EMBO J. 7(8): 2463–2473, 1988; GenBank Accession No. X12556) (SEQ ID NO: 5). In the cDNA of the present invention, the sequence on the 3' side of the 2919th base in GenBank/X12556 (SEQ ID NO: 5) is linked to the downstream side of the 2696th base in GenBank/X12556 (SEQ ID NO: 5) to induce a frame shift in amino acid translation (and eliminate bases 2697 to 2919 of SEQ ID NO: 5), creating the sequence shown in SEQ ID NO: 1. FIG. 1 shows the base sequence of the 2679th to 2952nd bases of the Dbl gene cDNA in its normal form (see bases 2679 to 2952 of SEQ ID NO: 5), the corresponding base sequence of the cDNA of the disease gene of RA (see bases 2679 to 2757 of SEQ ID NO: 1), and the respective amino acid sequences (1 letter notation) encoded by these sequences (see amino acid residues 836 to 860 of SEQ ID NO: 2 and amino acid residues 836 to 925 of SEQ ID NO: 6).

The cDNAs of the present invention may easily be isolated by, for example, the method described in the aftermentioned Example. Further, the cDNAs of the present invention may be cloned from a cDNA library produced by a known method (Mol. Cell. Biol. 2:161–170, 1982; J. Gene 25: 263–269, 1983; Gene 150: 243–250, 1994) using poly (A)+RNA extracted from cells of a patient with rheumatoid arthritis. Such cloning may be performed by, for example, synthesizing oligonucleotides based on the sequence information provided by the present invention and screening by colony or plaque hybridization by a known method using the resultant oligonucleotides as probes. Also, oligonucleotides, which hybridize to both ends of the target cDNA fragment, may be synthesized, and using them as primers, the cDNA of the present invention may be produced by RT-PCR method from mRNAs isolated from cells of a patient with rheumatoid arthritis.

The DNA fragment of the present invention comprises a portion of the aforesaid cDNA, and necessarily contains the base sequence from 2693rd to 2702nd of SEQ ID NO: 1. In other words, 2693rd to 2702nd of SEQ ID NO: 1 is the underlined sequence in FIG. 1, and is a characteristic region, which is not present in normal Dbl gene or its cDNAs. Further, the DNA fragment includes both sense and antisense strands. These DNA fragments may be used as probes for genetic diagnosis.

The proteins of the present invention are expression products resulting from the RA disease genes of the present invention, and has the amino acid sequence shown in SEQ ID NO: 2. These proteins may be obtained by chemical peptide synthesis method based on the amino acid sequence provided by the present application, or by recombinant DNA technique using cDNAs provided by the present application. For example, when recombinant DNA technique is used to obtain the proteins, RNA may be prepared by in vitro transcription using a vector containing the cDNA of the present invention; using this RNA as a template, the proteins may be obtained by in vitro translation. Also, the coding region of the cDNA may be recombined into an appropriate expression vector by any known method, and the recombinant vector obtained may be used to transform E. coli., Bacillus siibtilis, yeast, animal cells or the like, whereby expression of the protein in bulk would be possible using these recombinant cells.

When in vitro translation is used to produce the proteins of the present invention, the coding region of the cDNA of the present invention may be recombined into a vector with RNA polymerase promoter, and introduced into the in vitro translation system containing the RNA polymerase corresponding to the promoter, such as rabbit reticular erythrocyte lysate or wheat embryo extracts. T7, T3 and SP6 may be listed as examples of the RNA polymerase promoter. Examples of vectors, which contain any of these RNA polymerase promoters are pKA1, pCDM8, pT3/T7 18, pT7/3 19 and pBluescript II.

Furthermore, when the proteins of the present invention are expressed using microorganisms such as E. coli., a recombinant expression vector may be prepared by incorporating the coding region of the cDNA of the present invention into an expression vector which contains replication origin replicable in microorganism, promoter, ribosome-binding site, cDNA cloning site, terminator and the like, which is then used to transform a host cell and incubating the transformed cell. In such cases, by adding initiation and termination codons before and after an arbitrary coding region, protein fragments, which contain the arbitrary region may be obtained. Alternatively, the protein may be obtained as a fusion protein with another protein. By cleaving the fusion protein using an appropriate protease, the target protein may also be isolated. Examples of the expression vector for E. coli. are pUC system, pBluescript II, pET expression system and pGEX expression system.

When expressing the protein of the present invention in eucaryotic cells, the coding region of the inventive cDNA may be incorporated into an expression vector for eucaryotic cells that contains a promoter, a splicing region, a poly(A) addition site and the like, which may be introduced into eucaryotic cells. Such expression vectors may be pKA1, pCDM8, pSVK3, pMSG, pSVL, pBK-CMV, pBK-RSV, EBV vector, pRS and pYES2. Generally, mammal culture cells such as monkey kidney cell COS7 or Chinese hamster ovarian cell CHO, budding yeast, fission yeast, silkworm cells and *Xenopus laevis* o-site cells are used as eucaryotic cells, but in the present invention, they are not limited to these examples. To introduce the expression vector into eucaryotic cells, any known method such as electroporation, calcium phosphate method, liposome method, and DEAE dextran method may be used.

After the proteins are expressed in procaryotic or eucaryotic cells by the above-described methods, the protein of interest may be separated from the culture and purified by using combinations of known separation/purification methods. Examples are, treatment with degenerating agents such as urea or surfactant, ultrasonication, enzyme digestion, salt- or solvent-precipitation, dialysis, centrifugation, ultrafiltration, gel filtration, SDS-PAGE, isoelectric focusing method, ion-exchange chromatography, hydrophobic chromatography, affinity chromatography, reverse phase chromatography and the like.

Further, the protein of the present invention also encompasses fusion proteins of the present protein with other arbitrary protein.

The peptide of the present invention is a peptide fragment, which contains at least part (5 amino acid residues or more) of the amino acid sequence shown in SEQ ID NO: 2. Such peptide may be used as an antigen for preparing an antibody.

The antibody of the present invention may be obtained as a polyclonal or monoclonal antibody by any known method using the protein itself or a partial peptide thereof as antigen.

The method for diagnosing rheumatoid arthritis of the present invention may be performed, for example, by detecting the presence of characteristic mRNAs transcribed by RA disease gene in a biological specimen (body fluid, cell) obtained from a subject. Such mRNA may be detected by, for example, RT-PCR amplification of the mRNA containing the characteristic region (e.g., the underlined region in FIG. 1), or by in vitro or in situ hybridization analysis using any characteristic sequence region of the mRNA for RA disease gene as a probe.

Furthermore, the method for diagnosing rheumatoid arthritis of the present invention may also be performed by detecting the presence of protein(s) expressed from RA disease gene in a biological specimen of a subject. Such detection may be performed by, for example, enzyme immunoassay or radioimmunoassay using the antibody of the present invention. Further, the presence of such gene expression or protein may be detected by using any diagnosis kit; for example, hybridization analysis kit such as DNA chip and the like or immunoassay kit such as ELISA kit may be used.

The Dbl defect of the present invention may be complemented by, for example, protein or low molecular weight compounds.

EXAMPLES

Hereinafter, the RA disease gene of the present invention will be described in further detail through the following examples; however, the present invention is not limited to these examples.

Example 1

Identification of the RA Disease Gene

For the gene analysis by affected sib-pair analysis method using microsatellite marker, DNAs were prepared from peripheral blood collected from a family of two rheumatoid arthritis patients and one normal, by the guanidine-thiocyanate method (The Japan Society of Blood Transfusion Report 40(2), 413). Further, 11 markers (DXS1047, DXS8072, DXS8041, DXS8094, DXS1192, DXS1205, DXS1227, DXS8106, DX8043, DX8028 and DXS1200)

(Nature 360, 1996) were selected as microsatellite markers with heterozygosity higher than about 0.7, from the range of the candidate genetic loci previously disclosed by the present inventors (International Immunology 10 (12): 1891–1895; Journal of Clinical Rheumatology 4(3): 156–158, 1998), and fluorescence-labeled primers that could amplify each loci were synthesized at Perkin Elmer Inc. The sequences of the primer are disclosed in the above literature and are known. Each marker region was isolated by PCR under the following conditions. The reaction solution was prepared by mixing 5 pmol of primer, approximately 0.5 μg of template DNA, 1.5 μg of Buffer II (Perkin Elmer Inc.), 1.0 μl of 2 mM dNTP Mix (Perkin Elmer Inc.), 0.12 μl of Ampli Taq Gold enzyme (Perkin Elmer Inc.) and 0.9 μl of 25 mM MgCl$_2$ (Perkin Elmer Inc.), and adding sterilized water to obtain a total volume of 15 μl. The reaction was performed in a thermal cycler (PTC-200) of MJ Research Inc. First, one cycle of enzyme activation at 95° C. for 12 minute, 10 cycles of heat denaturation at 94° C. for one minute, primer annealing at 47° C. for one minute and extension at 72° C. for 2 minutes were performed, after which 20 cycles of heat denaturation at 89° C. for one minute, primer annealing at 47° C. for one minute and extension at 72° C. for 2 minutes were performed. Each of the resultant DNA fragments were analyzed in a DNA sequencer (Perkin Elmer Inc., Type AB1377) by subjecting to electrophoresis with size markers for Genescan (Perkin Elmer Inc.) of the manufacture's specification, and the DNA analysis was performed by using the attached softwares, Genescan and Genotyper. The data obtained were analyzed on Unix system using Mapmaker Sibs software (Am J Hum Genet, 57, 439–454, 1995), which is available to the public, for genetic linkage analysis, and the maximum Lod value was calculated by single point analysis.

As a result, the maximum Lod was determined to be 2.03 for DXS984, which is located in the 0.1 centi Morgan vicinity of DXS1232, one of the candidate genetic loci disclosed by the present inventors (International Immunology 10(12): 1891–1895; Journal of Clinical Rheumatology 4 (3): 156 –158, 1998), showing significant correlation. By searching the international data base on the internet (Genemap98, http://www.ncbi.nlm.nih.gov/genemap98/), it was found that the physical location of DXS984 was 4259 cR10000(F) on the G3 Radiation hybrid map, and thus it was proved that the protooncogene Dbl was situated nearest to DXS984.

Example 2

Analysis of Abnormal Dbl Gene

In order to compare the cDNAs between of Dbl genes, cDNA was synthesized by reverse transcription using RT-PCR kit (Perkin Elmer Inc.) from the total RNA obtained from peripheral blood of RA disease patients collected using Isogen agent (Nippongene Co. Ltd.), and dissolved in 20 μl of sterilized water. Furthermore, primers (SEQ ID NOs: 3 and 4) were prepared using the Dbl cDNA sequence (Genbank Accession No. X12556) (Amersham Pharmacia), and part of the Dbl cDNA sequence was isolated by the PCR method. The composition of the reaction solution for PCR was: 10 pmol each of forward primer (SEQ ID NO: 3) and reverse primer (SEQ ID NO: 4), approximately 0.1 μg of template DNA, 2.5 μl of LA-PCR buffer (Takara Shuzo Co. Ltd.), 4.0 μl of 2.5 mM dNTP Mix, 0.25 μl of LA Taq enzyme (Takara Shuzo Co. Ltd.) and 2.5 μl of 25 mM MgCl$_2$ mixed, after which sterilized water was added to obtain a total volume of 25 μl. The reaction was performed in a thermal cycler (PTC-200) of MJ Research by repeating 35 cycles of the process of heat denaturation at 94° C. for 30 seconds, primer annealing at 52° C. for 30 seconds and extension at 72° C. for 2 minutes. The PCR products were subjected to electrophoresis of conventional methods, in TAE buffer solution using 1% Agarose L (Nippongene Co. Ltd.) gel and DNA molecular weight markers (200 bp ladder) by Promega Co., to confirm the amplified bands. As a result, it was found that the size of normal DNA was 660 bp while the size of DNA chain from some patients were distinctly shorter (approximately 440 bp).

Next, after each respective bands were cut out, the gels were melted at 65° C. for 10 minutes, and the DNAs were purified by conventional phenol extraction methods and ethanol precipitation methods. Then, using 100 ng of the resultant DNA as a template, cycle sequence reaction and purification were performed following the specifications of the manufacturer of BigDye terminator cycle sequence kit by Perkin Elmer Inc., and the sequence was determined by a Type AB1377 DNA sequencer of Perkin Elmer Inc. As a result, it was evident that in the above-described abnormally short DNA, as shown in FIG. 1, the 223 bp from the number 2697 to number 2919 bases are deleted, making it 437 bp. This result indicates that with the amino acid deletion encoded in the genetic information downstream of base number 2693, and by inducing frame shift, abnormal polypeptide chain short of 65 amino acids is produced.

As described in detail above, the present invention provides a cDNA of a disease gene for rheumatoid arthritis occurring in human chromosome X. This invention enables the easy and reliable diagnosis of rheumatoid arthritis. Furthermore, this invention is useful for the development of novel treatment and therapeutic agents for rheumatoid arthritis.

What is claimed is:

1. A cDNA of a disease gene for rheumatoid arthritis, which comprises the nucleotide sequence of SEQ ID NO: 1.

2. A DNA fragment of SEQ ID NO: 1, wherein said DNA fragment comprises at least nucleotides 2693 to 2702 of SEQ ID NO: 1.

3. A polynucleotide, comprising the nucleotide sequence of SEQ ID NO:1.

4. A polynucleotide, consisting of a fragment of SEQ ID NO: 1, wherein said polynucleotide comprises at least nucleotides 2693 to 2702 of SEQ ID NO: 1.

5. The polynucleotide according to claim 4 which consists of nucleotides 2693 to 2702 of SEQ ID NO: 1.

* * * * *

SEQUENCE LISTING

```
<160> NUMBER OF SEQ ID NOS: 6

<210> SEQ ID NO 1
<211> LENGTH: 3429
<212> TYPE: DNA
<213> ORGANISM: Homo sapiens
<220> FEATURE:
<221> NAME/KEY: CDS
<222> LOCATION: (175)..(2757)
```

-continued

<223> OTHER INFORMATION: Mutant of Db1 cDNA in GenBank/X12556

<400> SEQUENCE: 1

| | | |
|---|---|---|
| tttttttttt ttcctcccaa cattgctgcc actgtgctaa tggaagcacc acggcagctt | 60 |
| tgtttgatag agatttttgg ctgccgtttt taaatactac ccaagaagca gctcgtattt | 120 |
| catcaatgtt gcgttgacaa ttggaaaaga aaagtgtaat tgcgtacagg cgaa atg | 177 |
| | Met | |
| | 1 | |

```
gca gaa gca aat ccc cgg aga ggc aag atg agg ttc aga agg aat gcg     225
Ala Glu Ala Asn Pro Arg Arg Gly Lys Met Arg Phe Arg Arg Asn Ala
            5                  10                  15 gct tcc ttc cct ggg aac ttg cac ttg gtt ttg gtt tta cgt cct acc     273
Ala Ser Phe Pro Gly Asn Leu His Leu Val Leu Val Leu Arg Pro Thr
        20                  25                  30 agc ttt ctt caa cga acg ttc aca gac att gga ttt tgg ttt agt cag     321
Ser Phe Leu Gln Arg Thr Phe Thr Asp Ile Gly Phe Trp Phe Ser Gln
    35                  40                  45 gag gat ttt atg cct aaa tta cca gtt gtt atg ctg agc tca gtt agt     369
Glu Asp Phe Met Pro Lys Leu Pro Val Val Met Leu Ser Ser Val Ser
50                  55                  60                  65 gat ttg ctg aca tac att gat gac aag caa tta acc cct gag tta ggc     417
Asp Leu Leu Thr Tyr Ile Asp Asp Lys Gln Leu Thr Pro Glu Leu Gly
                70                  75                  80 ggc acc ttg cag tac tgc cac agt gaa tgg atc atc ttc aga aat gct     465
Gly Thr Leu Gln Tyr Cys His Ser Glu Trp Ile Ile Phe Arg Asn Ala
            85                  90                  95 ata gaa aat ttt gcc ctc aca gtg aaa gaa atg gct cag atg tta cag    513
Ile Glu Asn Phe Ala Leu Thr Val Lys Glu Met Ala Gln Met Leu Gln
        100                 105                 110 tcc ttt gga act gaa ctg gct gag aca gaa cta cca gat gat att ccc    561
Ser Phe Gly Thr Glu Leu Ala Glu Thr Glu Leu Pro Asp Asp Ile Pro
    115                 120                 125 tca ata gaa gaa att ctg gca att cgt gct gaa agg tat cat ctg ttg    609
Ser Ile Glu Glu Ile Leu Ala Ile Arg Ala Glu Arg Tyr His Leu Leu
130                 135                 140                 145 aag aat gat att aca gct gta acc aaa gaa gga aaa att ctg cta aca    657
Lys Asn Asp Ile Thr Ala Val Thr Lys Glu Gly Lys Ile Leu Leu Thr
                150                 155                 160 aat ctg gaa gtg cct gac act gaa gga gct gtc agt tca aga cta gaa    705
Asn Leu Glu Val Pro Asp Thr Glu Gly Ala Val Ser Ser Arg Leu Glu
            165                 170                 175 tgt cat cgg caa ata agt ggt gac tgg caa act att aat aag ttg ctg    753
Cys His Arg Gln Ile Ser Gly Asp Trp Gln Thr Ile Asn Lys Leu Leu
        180                 185                 190 act caa gta cat gat atg gaa aca gct ttt gat gga ttt tgg gaa aaa    801
Thr Gln Val His Asp Met Glu Thr Ala Phe Asp Gly Phe Trp Glu Lys
    195                 200                 205 cat caa tta aaa atg gag cag tat ctg caa cta tgg aag ttt gag cag    849
His Gln Leu Lys Met Glu Gln Tyr Leu Gln Leu Trp Lys Phe Glu Gln
210                 215                 220                 225 gat ttt caa cag ctt gtg act gaa gtt gaa ttt cta tta aac caa caa    897
Asp Phe Gln Gln Leu Val Thr Glu Val Glu Phe Leu Leu Asn Gln Gln
                230                 235                 240 gca gaa ctg gct gat gta aca ggg act ata gct caa gta aaa caa aaa    945
Ala Glu Leu Ala Asp Val Thr Gly Thr Ile Ala Gln Val Lys Gln Lys
            245                 250                 255 ata aaa aaa ttg gaa aac tta gat gaa aat tct cag gag cta tta tca    993
Ile Lys Lys Leu Glu Asn Leu Asp Glu Asn Ser Gln Glu Leu Leu Ser
        260                 265                 270
```

-continued

```
aag gcc cag ttt gtg ata tta cat gga cac aag ctt gca gca aat cac   1041
Lys Ala Gln Phe Val Ile Leu His Gly His Lys Leu Ala Ala Asn His
    275                 280                 285 cat tat gca ctt gat tta atc tgc cag agg tgc aat gag cta cgt tac   1089
His Tyr Ala Leu Asp Leu Ile Cys Gln Arg Cys Asn Glu Leu Arg Tyr
290                 295                 300                 305 ctt tct gat att ttg gtt aat gag ata aaa gca aaa cgg ata caa ctc   1137
Leu Ser Asp Ile Leu Val Asn Glu Ile Lys Ala Lys Arg Ile Gln Leu
                310                 315                 320 agc agg acc ttc aaa atg cat aaa ctc cta cag cag gct cgt caa tgc   1185
Ser Arg Thr Phe Lys Met His Lys Leu Leu Gln Gln Ala Arg Gln Cys
            325                 330                 335 tgt gat gaa ggg gaa tgt cta gct aat cag gaa ata gat aag ttt       1233
Cys Asp Glu Gly Glu Cys Leu Leu Ala Asn Gln Glu Ile Asp Lys Phe
        340                 345                 350 cag tct aaa gaa gat gct cag aaa gct ctc caa gac att gaa aat ttt   1281
Gln Ser Lys Glu Asp Ala Gln Lys Ala Leu Gln Asp Ile Glu Asn Phe
    355                 360                 365 ctt gaa atg gct cta ccc ttt ata aat tat gaa cct gaa aca ctg cag   1329
Leu Glu Met Ala Leu Pro Phe Ile Asn Tyr Glu Pro Glu Thr Leu Gln
370                 375                 380                 385 tat gaa ttt gat gta ata tta tct cct gag ctt aag gtt caa atg aag   1377
Tyr Glu Phe Asp Val Ile Leu Ser Pro Glu Leu Lys Val Gln Met Lys
                390                 395                 400 act ata caa ctc aag ctt gaa aac att cga agt ata ttt gag aac cag   1425
Thr Ile Gln Leu Lys Leu Glu Asn Ile Arg Ser Ile Phe Glu Asn Gln
            405                 410                 415 cag gct ggt ttc agg aac ctg gca gat aag cat gtg agg cca atc caa   1473
Gln Ala Gly Phe Arg Asn Leu Ala Asp Lys His Val Arg Pro Ile Gln
        420                 425                 430 ttt gtg gta ccc aca cct gaa aat ttg gtc aca tct ggg aca cca ttt   1521
Phe Val Val Pro Thr Pro Glu Asn Leu Val Thr Ser Gly Thr Pro Phe
    435                 440                 445 ttt tca tct aaa caa ggg aag aag act tgg aga caa aat cag agc aac   1569
Phe Ser Ser Lys Gln Gly Lys Lys Thr Trp Arg Gln Asn Gln Ser Asn
450                 455                 460                 465 tta aaa att gaa gtg gtg cct gat tgt cag gag aag aga agt tct ggt   1617
Leu Lys Ile Glu Val Val Pro Asp Cys Gln Glu Lys Arg Ser Ser Gly
                470                 475                 480 cca tcc tcc agt ttg gac aat ggc aat agc ttg gat gtt tta aag aac   1665
Pro Ser Ser Ser Leu Asp Asn Gly Asn Ser Leu Asp Val Leu Lys Asn
            485                 490                 495 cac gta cta aat gaa ctg ata cag act gag aga gtt tat gtt cga gaa   1713
His Val Leu Asn Glu Leu Ile Gln Thr Glu Arg Val Tyr Val Arg Glu
        500                 505                 510 ctg tat act gtt ttg ttg ggt tat aga gcg gag atg gat aat cca gag   1761
Leu Tyr Thr Val Leu Leu Gly Tyr Arg Ala Glu Met Asp Asn Pro Glu
    515                 520                 525 atg ttt gat ctt atg cca cct ctc ctg aga aat aaa aag gac att ctc   1809
Met Phe Asp Leu Met Pro Pro Leu Leu Arg Asn Lys Lys Asp Ile Leu
530                 535                 540                 545 ttt gga aac atg gca gaa ata tat gaa ttc cat aac gac att ttc ttg   1857
Phe Gly Asn Met Ala Glu Ile Tyr Glu Phe His Asn Asp Ile Phe Leu
                550                 555                 560 agc agc ctg gaa aat tgt gct cat gct cca gaa aga gtg gga cct tgt   1905
Ser Ser Leu Glu Asn Cys Ala His Ala Pro Glu Arg Val Gly Pro Cys
            565                 570                 575 ttc ctg gaa agg aag gat gat ttt cag atg tat gca aaa tat tgt cag   1953
Phe Leu Glu Arg Lys Asp Asp Phe Gln Met Tyr Ala Lys Tyr Cys Gln
        580                 585                 590
```

-continued

```
aat aag ccc aga tca gaa aca att tgg agg aag tat tca gaa tgc gca      2001
Asn Lys Pro Arg Ser Glu Thr Ile Trp Arg Lys Tyr Ser Glu Cys Ala
    595                 600                 605 ttt ttc cag gaa tgt caa aga aag tta aaa cac aga ctt aga ctg gat      2049
Phe Phe Gln Glu Cys Gln Arg Lys Leu Lys His Arg Leu Arg Leu Asp
610                 615                 620                 625 tcc tat tta ctc aaa cca gtg caa cga atc act aaa tat cag tta ttg      2097
Ser Tyr Leu Leu Lys Pro Val Gln Arg Ile Thr Lys Tyr Gln Leu Leu
                630                 635                 640 ttg aag gag cta tta aaa tat agc aaa gac tgt gaa ggt tct gct ctg      2145
Leu Lys Glu Leu Leu Lys Tyr Ser Lys Asp Cys Glu Gly Ser Ala Leu
            645                 650                 655 ttg aag aag gca ctc gat gca atg ctg gat tta ctg aag tca gtt aat      2193
Leu Lys Lys Ala Leu Asp Ala Met Leu Asp Leu Leu Lys Ser Val Asn
        660                 665                 670 gat tct atg cat cag att gca ata aat ggc tat att gga aac tta aat      2241
Asp Ser Met His Gln Ile Ala Ile Asn Gly Tyr Ile Gly Asn Leu Asn
    675                 680                 685 gaa ctg ggc aag atg ata atg caa ggt gga ttc agc gtt tgg ata ggg      2289
Glu Leu Gly Lys Met Ile Met Gln Gly Gly Phe Ser Val Trp Ile Gly
690                 695                 700                 705 cac aag aaa ggt gct aca aaa atg aag gat ttg gct aga ttc aaa cca      2337
His Lys Lys Gly Ala Thr Lys Met Lys Asp Leu Ala Arg Phe Lys Pro
                710                 715                 720 atg cag cga cac ctt ttc ttg tat gaa aaa gcc att gtt ttt tgc aaa      2385
Met Gln Arg His Leu Phe Leu Tyr Glu Lys Ala Ile Val Phe Cys Lys
            725                 730                 735 agg cgt gtt gaa agt gga gaa ggc tct gac aga tac ccg tca tac agt      2433
Arg Arg Val Glu Ser Gly Glu Gly Ser Asp Arg Tyr Pro Ser Tyr Ser
        740                 745                 750 ttt aaa cac tgt tgg aaa atg gat gaa gtt gga atc act gaa tat gta      2481
Phe Lys His Cys Trp Lys Met Asp Glu Val Gly Ile Thr Glu Tyr Val
    755                 760                 765 aaa ggt gat aac cgc aag ttt gaa atc tgg tat ggt gaa aag gaa gaa      2529
Lys Gly Asp Asn Arg Lys Phe Glu Ile Trp Tyr Gly Glu Lys Glu Glu
770                 775                 780                 785 gtt tat att gtc cag gct tct aat gta gat gtg aag atg acg tgg cta      2577
Val Tyr Ile Val Gln Ala Ser Asn Val Asp Val Lys Met Thr Trp Leu
                790                 795                 800 aaa gaa ata aga aat att ttg ttg aag cag cag gaa ctt ttg aca gtt      2625
Lys Glu Ile Arg Asn Ile Leu Leu Lys Gln Gln Glu Leu Leu Thr Val
            805                 810                 815 aaa aaa aga aag caa cag gat caa tta aca gaa cgg gat aag ttt cag      2673
Lys Lys Arg Lys Gln Gln Asp Gln Leu Thr Glu Arg Asp Lys Phe Gln
        820                 825                 830 att tct ctt cag cag aat gat gaa gac ctg tgt cgg aga tgg ctc tcc      2721
Ile Ser Leu Gln Gln Asn Asp Glu Asp Leu Cys Arg Arg Trp Leu Ser
    835                 840                 845 tat att gat gaa gct act atg tca aat ggc aag tag ctctttcctg          2767
Tyr Ile Asp Glu Ala Thr Met Ser Asn Gly Lys
850                 855                 860 cctgcttctc agctcatttg gaaaaatact gcgcaaaaga cattgagctc aaatgatgca    2827
gatgttgttt tcaggttaat ggacacgcaa agaaaccaca gcacatactt cttttcttc     2887 atttaataaa gcttttaatt atggtacgct gtcttttaa aatcatgtat ttaatgtgtc     2947
agatattgtg cttgaaagat tctcatctca gaatactttt ggacttgaaa attatttctt   3007
ctctactttg taaccaaatg caatcggtgt gccttggatt atttagttta ttaatgaatt   3067
```

-continued

```
aagtcaaaat tacggctgca aaatggctaa ggtcaagtaa agcacaacat tatgatttaa   3127
tatgcttttg ttgaaaccac agcttttgtg cccattgttt taacttgtgt gaaacaatac   3187
aaagcccaga aattcttttc ggggcatgag taaattttgt tcagggctac tgtctgtatg   3247
tgcccagata aaattttcat gagagtagtt tacaaaagcc gtatttaaaa gttaatattt   3307
tcacactttt tttctggatt tctgcttata attaatgtaa cttaaattag ttgtgctctg   3367
ctattttctg tatatttcat gttgtaattc ttttttttcaa ataaaaatta attcttcagg   3427
tt                                                                   3429
```

<210> SEQ ID NO 2
<211> LENGTH: 860
<212> TYPE: PRT
<213> ORGANISM: Homo sapiens

<400> SEQUENCE: 2

```
Met Ala Glu Ala Asn Pro Arg Arg Gly Lys Met Arg Phe Arg Arg Asn
 1               5                  10                  15

Ala Ala Ser Phe Pro Gly Asn Leu His Leu Val Leu Val Leu Arg Pro
            20                  25                  30

Thr Ser Phe Leu Gln Arg Thr Phe Thr Asp Ile Gly Phe Trp Phe Ser
        35                  40                  45

Gln Glu Asp Phe Met Pro Lys Leu Pro Val Val Met Leu Ser Ser Val
    50                  55                  60

Ser Asp Leu Leu Thr Tyr Ile Asp Asp Lys Gln Leu Thr Pro Glu Leu
65                  70                  75                  80

Gly Gly Thr Leu Gln Tyr Cys His Ser Glu Trp Ile Ile Phe Arg Asn
                85                  90                  95

Ala Ile Glu Asn Phe Ala Leu Thr Val Lys Glu Met Ala Gln Met Leu
            100                 105                 110

Gln Ser Phe Gly Thr Glu Leu Ala Glu Thr Glu Leu Pro Asp Asp Ile
        115                 120                 125

Pro Ser Ile Glu Glu Ile Leu Ala Ile Arg Ala Glu Arg Tyr His Leu
    130                 135                 140

Leu Lys Asn Asp Ile Thr Ala Val Thr Lys Glu Gly Lys Ile Leu Leu
145                 150                 155                 160

Thr Asn Leu Glu Val Pro Asp Thr Glu Gly Ala Val Ser Ser Arg Leu
                165                 170                 175

Glu Cys His Arg Gln Ile Ser Gly Asp Trp Gln Thr Ile Asn Lys Leu
            180                 185                 190

Leu Thr Gln Val His Asp Met Glu Thr Ala Phe Asp Gly Phe Trp Glu
        195                 200                 205

Lys His Gln Leu Lys Met Glu Gln Tyr Leu Gln Leu Trp Lys Phe Glu
    210                 215                 220

Gln Asp Phe Gln Gln Leu Val Thr Glu Val Glu Phe Leu Leu Asn Gln
225                 230                 235                 240

Gln Ala Glu Leu Ala Asp Val Thr Gly Thr Ile Ala Gln Val Lys Gln
                245                 250                 255

Lys Ile Lys Lys Leu Glu Asn Leu Asp Glu Asn Ser Gln Glu Leu Leu
            260                 265                 270

Ser Lys Ala Gln Phe Val Ile Leu His Gly His Lys Leu Ala Ala Asn
        275                 280                 285

His His Tyr Ala Leu Asp Leu Ile Cys Gln Arg Cys Asn Glu Leu Arg
    290                 295                 300
```

```
Tyr Leu Ser Asp Ile Leu Val Asn Glu Ile Lys Ala Lys Arg Ile Gln
305                 310                 315                 320

Leu Ser Arg Thr Phe Lys Met His Lys Leu Leu Gln Gln Ala Arg Gln
                325                 330                 335

Cys Cys Asp Glu Gly Glu Cys Leu Leu Ala Asn Gln Glu Ile Asp Lys
            340                 345                 350

Phe Gln Ser Lys Glu Asp Ala Gln Lys Ala Leu Gln Asp Ile Glu Asn
        355                 360                 365

Phe Leu Glu Met Ala Leu Pro Phe Ile Asn Tyr Glu Pro Glu Thr Leu
    370                 375                 380

Gln Tyr Glu Phe Asp Val Ile Leu Ser Pro Glu Leu Lys Val Gln Met
385                 390                 395                 400

Lys Thr Ile Gln Leu Lys Leu Glu Asn Ile Arg Ser Ile Phe Glu Asn
                405                 410                 415

Gln Gln Ala Gly Phe Arg Asn Leu Ala Asp Lys His Val Arg Pro Ile
            420                 425                 430

Gln Phe Val Val Pro Thr Pro Glu Asn Leu Val Thr Ser Gly Thr Pro
        435                 440                 445

Phe Phe Ser Ser Lys Gln Gly Lys Lys Thr Trp Arg Gln Asn Gln Ser
    450                 455                 460

Asn Leu Lys Ile Glu Val Val Pro Asp Cys Gln Glu Lys Arg Ser Ser
465                 470                 475                 480

Gly Pro Ser Ser Ser Leu Asp Asn Gly Asn Ser Leu Asp Val Leu Lys
                485                 490                 495

Asn His Val Leu Asn Glu Leu Ile Gln Thr Glu Arg Val Tyr Val Arg
            500                 505                 510

Glu Leu Tyr Thr Val Leu Leu Gly Tyr Arg Ala Glu Met Asp Asn Pro
        515                 520                 525

Glu Met Phe Asp Leu Met Pro Pro Leu Leu Arg Asn Lys Lys Asp Ile
    530                 535                 540

Leu Phe Gly Asn Met Ala Glu Ile Tyr Glu Phe His Asn Asp Ile Phe
545                 550                 555                 560

Leu Ser Ser Leu Glu Asn Cys Ala His Ala Pro Glu Arg Val Gly Pro
                565                 570                 575

Cys Phe Leu Glu Arg Lys Asp Asp Phe Gln Met Tyr Ala Lys Tyr Cys
            580                 585                 590

Gln Asn Lys Pro Arg Ser Glu Thr Ile Trp Arg Lys Tyr Ser Glu Cys
        595                 600                 605

Ala Phe Phe Gln Glu Cys Gln Arg Lys Leu Lys His Arg Leu Arg Leu
    610                 615                 620

Asp Ser Tyr Leu Leu Lys Pro Val Gln Arg Ile Thr Lys Tyr Gln Leu
625                 630                 635                 640

Leu Leu Lys Glu Leu Leu Lys Tyr Ser Lys Asp Cys Glu Gly Ser Ala
                645                 650                 655

Leu Leu Lys Lys Ala Leu Asp Ala Met Leu Asp Leu Leu Lys Ser Val
            660                 665                 670

Asn Asp Ser Met His Gln Ile Ala Ile Asn Gly Tyr Ile Gly Asn Leu
        675                 680                 685

Asn Glu Leu Gly Lys Met Ile Met Gln Gly Gly Phe Ser Val Trp Ile
    690                 695                 700

Gly His Lys Lys Gly Ala Thr Lys Met Lys Asp Leu Ala Arg Phe Lys
705                 710                 715                 720

Pro Met Gln Arg His Leu Phe Leu Tyr Glu Lys Ala Ile Val Phe Cys
```

```
                      725             730                 735
Lys Arg Arg Val Glu Ser Gly Glu Gly Ser Asp Arg Tyr Pro Ser Tyr
                740             745                 750

Ser Phe Lys His Cys Trp Lys Met Asp Glu Val Gly Ile Thr Glu Tyr
                755             760                 765

Val Lys Gly Asp Asn Arg Lys Phe Glu Ile Trp Tyr Gly Glu Lys Glu
        770             775                 780

Glu Val Tyr Ile Val Gln Ala Ser Asn Val Asp Val Lys Met Thr Trp
785                 790                 795                 800

Leu Lys Glu Ile Arg Asn Ile Leu Leu Lys Gln Gln Glu Leu Leu Thr
                    805             810                 815

Val Lys Lys Arg Lys Gln Gln Asp Gln Leu Thr Glu Arg Asp Lys Phe
                820             825                 830

Gln Ile Ser Leu Gln Gln Asn Asp Glu Asp Leu Cys Arg Arg Trp Leu
                835             840                 845

Ser Tyr Ile Asp Glu Ala Thr Met Ser Asn Gly Lys
                850             855                 860

<210> SEQ ID NO 3
<211> LENGTH: 19
<212> TYPE: DNA
<213> ORGANISM: Artificial sequence
<220> FEATURE:
<223> OTHER INFORMATION: Synthesized oligonucleotide

<400> SEQUENCE: 3
ggctagattc aaaccaatg                                                19

<210> SEQ ID NO 4
<211> LENGTH: 17
<212> TYPE: DNA
<213> ORGANISM: Artificial sequence
<220> FEATURE:
<223> OTHER INFORMATION: Synthesized oligonucleotide

<400> SEQUENCE: 4
gctacttgcc atttgac                                                  17

<210> SEQ ID NO 5
<211> LENGTH: 3652
<212> TYPE: DNA
<213> ORGANISM: Homo sapiens
<220> FEATURE:
<221> NAME/KEY: CDS
<222> LOCATION: (175)..(2952)
<223> OTHER INFORMATION: Dbl cDNA in GenBank/X12556

<400> SEQUENCE: 5 ttttttttt  tcctcccaa cattgctgcc actgtgctaa tggaagcacc acggcagctt      60
tgtttgatag agatttttgg ctgccgtttt taaatactac ccaagaagca gctcgtattt    120
catcaatgtt gcgttgacaa ttggaaaaga aaagtgtaat tgcgtacagg cgaa atg     177
                                                              Met
                                                               1 gca gaa gca aat ccc cgg aga ggc aag atg agg ttc aga agg aat gcg   225
Ala Glu Ala Asn Pro Arg Arg Gly Lys Met Arg Phe Arg Arg Asn Ala
        5                  10                  15 gct tcc ttc cct ggg aac ttg cac ttg gtt ttg gtt tta cgt cct acc   273
Ala Ser Phe Pro Gly Asn Leu His Leu Val Leu Val Leu Arg Pro Thr
    20                  25                  30 agc ttt ctt caa cga acg ttc aca gac att gga ttt tgg ttt agt cag   321
```

```
Ser Phe Leu Gln Arg Thr Phe Thr Asp Ile Gly Phe Trp Ser Gln
 35                  40                  45 gag gat ttt atg cct aaa tta cca gtt gtt atg ctg agc tca gtt agt        369
Glu Asp Phe Met Pro Lys Leu Pro Val Val Met Leu Ser Ser Val Ser
 50                  55                  60                  65 gat ttg ctg aca tac att gat gac aag caa tta acc cct gag tta ggc        417
Asp Leu Leu Thr Tyr Ile Asp Asp Lys Gln Leu Thr Pro Glu Leu Gly
                 70                  75                  80 ggc acc ttg cag tac tgc cac agt gaa tgg atc atc ttc aga aat gct        465
Gly Thr Leu Gln Tyr Cys His Ser Glu Trp Ile Ile Phe Arg Asn Ala
             85                  90                  95 ata gaa aat ttt gcc ctc aca gtg aaa gaa atg gct cag atg tta cag        513
Ile Glu Asn Phe Ala Leu Thr Val Lys Glu Met Ala Gln Met Leu Gln
         100                 105                 110 tcc ttt gga act gaa ctg gct gag aca gaa cta cca gat gat att ccc        561
Ser Phe Gly Thr Glu Leu Ala Glu Thr Glu Leu Pro Asp Asp Ile Pro
     115                 120                 125 tca ata gaa gaa att ctg gca att cgt gct gaa agg tat cat ctg ttg        609
Ser Ile Glu Glu Ile Leu Ala Ile Arg Ala Glu Arg Tyr His Leu Leu
130                 135                 140                 145 aag aat gat att aca gct gta acc aaa gaa gga aaa att ctg cta aca        657
Lys Asn Asp Ile Thr Ala Val Thr Lys Glu Gly Lys Ile Leu Leu Thr
                 150                 155                 160 aat ctg gaa gtg cct gac act gaa gga gct gtc agt tca aga cta gaa        705
Asn Leu Glu Val Pro Asp Thr Glu Gly Ala Val Ser Ser Arg Leu Glu
             165                 170                 175 tgt cat cgg caa ata agt ggt gac tgg caa act att aat aag ttg ctg        753
Cys His Arg Gln Ile Ser Gly Asp Trp Gln Thr Ile Asn Lys Leu Leu
         180                 185                 190 act caa gta cat gat atg gaa aca gct ttt gat gga ttt tgg gaa aaa        801
Thr Gln Val His Asp Met Glu Thr Ala Phe Asp Gly Phe Trp Glu Lys
     195                 200                 205 cat caa tta aaa atg gag cag tat ctg caa cta tgg aag ttt gag cag        849
His Gln Leu Lys Met Glu Gln Tyr Leu Gln Leu Trp Lys Phe Glu Gln
210                 215                 220                 225 gat ttt caa cag ctt gtg act gaa gtt gaa ttt cta tta aac caa caa        897
Asp Phe Gln Gln Leu Val Thr Glu Val Glu Phe Leu Leu Asn Gln Gln
                 230                 235                 240 gca gaa ctg gct gat gta aca ggg act ata gct caa gta aaa caa aaa        945
Ala Glu Leu Ala Asp Val Thr Gly Thr Ile Ala Gln Val Lys Gln Lys
             245                 250                 255 ata aaa aaa ttg gaa aac tta gat gaa aat tct cag gag cta tta tca        993
Ile Lys Lys Leu Glu Asn Leu Asp Glu Asn Ser Gln Glu Leu Leu Ser
         260                 265                 270 aag gcc cag ttt gtg ata tta cat gga cac aag ctt gca gca aat cac       1041
Lys Ala Gln Phe Val Ile Leu His Gly His Lys Leu Ala Ala Asn His
     275                 280                 285 cat tat gca ctt gat tta atc tgc cag agg tgc aat gag cta cgt tac       1089
His Tyr Ala Leu Asp Leu Ile Cys Gln Arg Cys Asn Glu Leu Arg Tyr
290                 295                 300                 305 ctt tct gat att ttg gtt aat gag ata aaa gca aaa cgg ata caa ctc       1137
Leu Ser Asp Ile Leu Val Asn Glu Ile Lys Ala Lys Arg Ile Gln Leu
                 310                 315                 320 agc agg acc ttc aaa atg cat aaa ctc cta cag cag gct cgt caa tgc       1185
Ser Arg Thr Phe Lys Met His Lys Leu Leu Gln Gln Ala Arg Gln Cys
             325                 330                 335 tgt gat gaa ggg gaa tgt ctt cta gct aat cag gaa ata gat aag ttt       1233
Cys Asp Glu Gly Glu Cys Leu Leu Ala Asn Gln Glu Ile Asp Lys Phe
         340                 345                 350
```

```
cag tct aaa gaa gat gct cag aaa gct ctc caa gac att gaa aat ttt    1281
Gln Ser Lys Glu Asp Ala Gln Lys Ala Leu Gln Asp Ile Glu Asn Phe
355                 360                 365 ctt gaa atg gct cta ccc ttt ata aat tat gaa cct gaa aca ctg cag    1329
Leu Glu Met Ala Leu Pro Phe Ile Asn Tyr Glu Pro Glu Thr Leu Gln
370                 375                 380                 385 tat gaa ttt gat gta ata tta tct cct gag ctt aag gtt caa atg aag    1377
Tyr Glu Phe Asp Val Ile Leu Ser Pro Glu Leu Lys Val Gln Met Lys
                390                 395                 400 act ata caa ctc aag ctt gaa aac att cga agt ata ttt gag aac cag    1425
Thr Ile Gln Leu Lys Leu Glu Asn Ile Arg Ser Ile Phe Glu Asn Gln
            405                 410                 415 cag gct ggt ttc agg aac ctg gca gat aag cat gtg agg cca atc caa    1473
Gln Ala Gly Phe Arg Asn Leu Ala Asp Lys His Val Arg Pro Ile Gln
        420                 425                 430 ttt gtg gta ccc aca cct gaa aat ttg gtc aca tct ggg aca cca ttt    1521
Phe Val Val Pro Thr Pro Glu Asn Leu Val Thr Ser Gly Thr Pro Phe
    435                 440                 445 ttt tca tct aaa caa ggg aag aag act tgg aga caa aat cag agc aac    1569
Phe Ser Ser Lys Gln Gly Lys Lys Thr Trp Arg Gln Asn Gln Ser Asn
450                 455                 460                 465 tta aaa att gaa gtg gtg cct gat tgt cag gag aag aga agt tct ggt    1617
Leu Lys Ile Glu Val Val Pro Asp Cys Gln Glu Lys Arg Ser Ser Gly
                470                 475                 480 cca tcc tcc agt ttg gac aat ggc aat agc ttg gat gtt tta aag aac    1665
Pro Ser Ser Ser Leu Asp Asn Gly Asn Ser Leu Asp Val Leu Lys Asn
            485                 490                 495 cac gta cta aat gaa ctg ata cag act gag aga gtt tat gtt cga gaa    1713
His Val Leu Asn Glu Leu Ile Gln Thr Glu Arg Val Tyr Val Arg Glu
        500                 505                 510 ctg tat act gtt ttg ttg ggt tat aga gcg gag atg gat aat cca gag    1761
Leu Tyr Thr Val Leu Leu Gly Tyr Arg Ala Glu Met Asp Asn Pro Glu
    515                 520                 525 atg ttt gat ctt atg cca cct ctc ctg aga aat aaa aag gac att ctc    1809
Met Phe Asp Leu Met Pro Pro Leu Leu Arg Asn Lys Lys Asp Ile Leu
530                 535                 540                 545 ttt gga aac atg gca gaa ata tat gaa ttc cat aac gac att ttc ttg    1857
Phe Gly Asn Met Ala Glu Ile Tyr Glu Phe His Asn Asp Ile Phe Leu
                550                 555                 560 agc agc ctg gaa aat tgt gct cat gct cca gaa aga gtg gga cct tgt    1905
Ser Ser Leu Glu Asn Cys Ala His Ala Pro Glu Arg Val Gly Pro Cys
            565                 570                 575 ttc ctg gaa agg aag gat gat ttt cag atg tat gca aaa tat tgt cag    1953
Phe Leu Glu Arg Lys Asp Asp Phe Gln Met Tyr Ala Lys Tyr Cys Gln
        580                 585                 590 aat aag ccc aga tca gaa aca att tgg agg aag tat tca gaa tgc gca    2001
Asn Lys Pro Arg Ser Glu Thr Ile Trp Arg Lys Tyr Ser Glu Cys Ala
    595                 600                 605 ttt ttc cag gaa tgt caa aga aag tta aaa cac aga ctt aga ctg gat    2049
Phe Phe Gln Glu Cys Gln Arg Lys Leu Lys His Arg Leu Arg Leu Asp
610                 615                 620                 625 tcc tat tta ctc aaa cca gtg caa cga atc act aaa tat cag tta ttg    2097
Ser Tyr Leu Leu Lys Pro Val Gln Arg Ile Thr Lys Tyr Gln Leu Leu
                630                 635                 640 ttg aag gag cta tta aaa tat agc aaa gac tgt gaa ggt tct gct ctg    2145
Leu Lys Glu Leu Leu Lys Tyr Ser Lys Asp Cys Glu Gly Ser Ala Leu
            645                 650                 655 ttg aag aag gca ctc gat gca atg ctg gat tta ctg aag tca gtt aat    2193
Leu Lys Lys Ala Leu Asp Ala Met Leu Asp Leu Leu Lys Ser Val Asn
        660                 665                 670
```

-continued

```
gat tct atg cat cag att gca ata aat ggc tat att gga aac tta aat       2241
Asp Ser Met His Gln Ile Ala Ile Asn Gly Tyr Ile Gly Asn Leu Asn
    675                 680                 685 gaa ctg ggc aag atg ata atg caa ggt gga ttc agc gtt tgg ata ggg       2289
Glu Leu Gly Lys Met Ile Met Gln Gly Gly Phe Ser Val Trp Ile Gly
690                 695                 700                 705 cac aag aaa ggt gct aca aaa atg aag gat ttg gct aga ttc aaa cca       2337
His Lys Lys Gly Ala Thr Lys Met Lys Asp Leu Ala Arg Phe Lys Pro
                710                 715                 720 atg cag cga cac ctt ttc ttg tat gaa aaa gcc att gtt ttt tgc aaa       2385
Met Gln Arg His Leu Phe Leu Tyr Glu Lys Ala Ile Val Phe Cys Lys
                    725                 730                 735 agg cgt gtt gaa agt gga gaa ggc tct gac aga tac ccg tca tac agt       2433
Arg Arg Val Glu Ser Gly Glu Gly Ser Asp Arg Tyr Pro Ser Tyr Ser
            740                 745                 750 ttt aaa cac tgt tgg aaa atg gat gaa gtt gga atc act gaa tat gta       2481
Phe Lys His Cys Trp Lys Met Asp Glu Val Gly Ile Thr Glu Tyr Val
        755                 760                 765 aaa ggt gat aac cgc aag ttt gaa atc tgg tat ggt gaa aag gaa gaa       2529
Lys Gly Asp Asn Arg Lys Phe Glu Ile Trp Tyr Gly Glu Lys Glu Glu
770                 775                 780                 785 gtt tat att gtc cag gct tct aat gta gat gtg aag atg acg tgg cta       2577
Val Tyr Ile Val Gln Ala Ser Asn Val Asp Val Lys Met Thr Trp Leu
                790                 795                 800 aaa gaa ata aga aat att ttg ttg aag cag cag gaa ctt ttg aca gtt       2625
Lys Glu Ile Arg Asn Ile Leu Leu Lys Gln Gln Glu Leu Leu Thr Val
                    805                 810                 815 aaa aaa aga aag caa cag gat caa tta aca gaa cgg gat aag ttt cag       2673
Lys Lys Arg Lys Gln Gln Asp Gln Leu Thr Glu Arg Asp Lys Phe Gln
            820                 825                 830 att tct ctt cag cag aat gat gaa aag caa cag gga gct ttt ata agt       2721
Ile Ser Leu Gln Gln Asn Asp Glu Lys Gln Gln Gly Ala Phe Ile Ser
        835                 840                 845 act gag gaa act gaa ttg gaa cac acc agc act gtg gtg gag gtc tgt       2769
Thr Glu Glu Thr Glu Leu Glu His Thr Ser Thr Val Val Glu Val Cys
850                 855                 860                 865 gag gca att gcg tca gtt cag gca gaa gca aat aca gtt tgg act gag       2817
Glu Ala Ile Ala Ser Val Gln Ala Glu Ala Asn Thr Val Trp Thr Glu
                870                 875                 880 gca tca caa tct gta gaa atc tct gaa gaa cct gcg gaa tgg tca agc       2865
Ala Ser Gln Ser Val Glu Ile Ser Glu Glu Pro Ala Glu Trp Ser Ser
                    885                 890                 895 aac tat ttc tac ccc act tat gat gaa aat gaa gaa gaa aat agg ccc       2913
Asn Tyr Phe Tyr Pro Thr Tyr Asp Glu Asn Glu Glu Glu Asn Arg Pro
            900                 905                 910 ctc atg aga cct gtg tcg gag atg gct ctc cta tat tga tgaagctact       2962
Leu Met Arg Pro Val Ser Glu Met Ala Leu Leu Tyr
        915                 920                 925 atgtcaaatg caagtagct ctttcctgcc tgcttctcag ctcatttgga aaaatactgc    3022
gcaaaagaca ttgagctcaa atgatgcaga tgttgttttc aggttaatgg acacgcaaag    3082
aaaccacagc acatacttct tttctttcat ttaataaagc ttttaattat ggtacgctgt    3142 cttttttaaaa tcatgtattt aatgtgtcag atattgtgct tgaaagattc tcatctcaga    3202
atacttttgg acttgaaaat tatttcttct ctactttgta accaaatgca atcggtgtgc    3262
cttggattat ttagttttatt aatgaattaa gtcaaaatta cggctgcaaa atggctaagg    3322
tcaagtaaag cacaacatta tgatttaata tgcttttgtt gaaaccacag cttttgtgcc    3382
```

-continued

```
cattgtttta acttgtgtga aacaatacaa agcccagaaa ttcttttcgg ggcatgagta      3442
aattttgttc agggctactg tctgtatgtg cccagataaa attttcatga gagtagttta      3502
caaaagccgt atttaaaagt taatattttc acacttttttt tctggatttc tgcttataat     3562
taatgtaact taaattagtt gtgctctgct attttctgta tatttcatgt tgtaattctt      3622
tttttcaaat aaaaattaat tcttcaggtt                                       3652
```

<210> SEQ ID NO 6
<211> LENGTH: 925
<212> TYPE: PRT
<213> ORGANISM: Homo sapiens

<400> SEQUENCE: 6

```
Met Ala Glu Ala Asn Pro Arg Arg Gly Lys Met Arg Phe Arg Arg Asn
 1               5                  10                  15

Ala Ala Ser Phe Pro Gly Asn Leu His Leu Val Leu Val Leu Arg Pro
             20                  25                  30

Thr Ser Phe Leu Gln Arg Thr Phe Thr Asp Ile Gly Phe Trp Phe Ser
         35                  40                  45

Gln Glu Asp Phe Met Pro Lys Leu Pro Val Val Met Leu Ser Ser Val
     50                  55                  60

Ser Asp Leu Leu Thr Tyr Ile Asp Asp Lys Gln Leu Thr Pro Glu Leu
 65                  70                  75                  80

Gly Gly Thr Leu Gln Tyr Cys His Ser Glu Trp Ile Ile Phe Arg Asn
                 85                  90                  95

Ala Ile Glu Asn Phe Ala Leu Thr Val Lys Glu Met Ala Gln Met Leu
            100                 105                 110

Gln Ser Phe Gly Thr Glu Leu Ala Glu Thr Glu Leu Pro Asp Asp Ile
        115                 120                 125

Pro Ser Ile Glu Glu Ile Leu Ala Ile Arg Ala Glu Arg Tyr His Leu
    130                 135                 140

Leu Lys Asn Asp Ile Thr Ala Val Thr Lys Glu Gly Lys Ile Leu Leu
145                 150                 155                 160

Thr Asn Leu Glu Val Pro Asp Thr Glu Gly Ala Val Ser Ser Arg Leu
                165                 170                 175

Glu Cys His Arg Gln Ile Ser Gly Asp Trp Gln Thr Ile Asn Lys Leu
            180                 185                 190

Leu Thr Gln Val His Asp Met Glu Thr Ala Phe Asp Gly Phe Trp Glu
        195                 200                 205

Lys His Gln Leu Lys Met Glu Gln Tyr Leu Gln Leu Trp Lys Phe Glu
    210                 215                 220

Gln Asp Phe Gln Gln Leu Val Thr Glu Val Glu Phe Leu Leu Asn Gln
225                 230                 235                 240

Gln Ala Glu Leu Ala Asp Val Thr Gly Thr Ile Ala Gln Val Lys Gln
                245                 250                 255

Lys Ile Lys Lys Leu Glu Asn Leu Asp Glu Asn Ser Gln Glu Leu Leu
            260                 265                 270

Ser Lys Ala Gln Phe Val Ile Leu His Gly His Lys Leu Ala Ala Asn
        275                 280                 285

His His Tyr Ala Leu Asp Leu Ile Cys Gln Arg Cys Asn Glu Leu Arg
    290                 295                 300

Tyr Leu Ser Asp Ile Leu Val Asn Glu Ile Lys Ala Lys Arg Ile Gln
305                 310                 315                 320

Leu Ser Arg Thr Phe Lys Met His Lys Leu Leu Gln Gln Ala Arg Gln
```

```
                    325                 330                 335
Cys Cys Asp Glu Gly Glu Cys Leu Leu Ala Asn Gln Glu Ile Asp Lys
                340                 345                 350

Phe Gln Ser Lys Glu Asp Ala Gln Lys Ala Leu Gln Asp Ile Glu Asn
                355                 360                 365

Phe Leu Glu Met Ala Leu Pro Phe Ile Asn Tyr Glu Pro Glu Thr Leu
                370                 375                 380

Gln Tyr Glu Phe Asp Val Ile Leu Ser Pro Glu Leu Lys Val Gln Met
385                 390                 395                 400

Lys Thr Ile Gln Leu Lys Leu Glu Asn Ile Arg Ser Ile Phe Glu Asn
                405                 410                 415

Gln Gln Ala Gly Phe Arg Asn Leu Ala Asp Lys His Val Arg Pro Ile
                420                 425                 430

Gln Phe Val Val Pro Thr Pro Glu Asn Leu Val Thr Ser Gly Thr Pro
                435                 440                 445

Phe Phe Ser Ser Lys Gln Gly Lys Lys Thr Trp Arg Gln Asn Gln Ser
                450                 455                 460

Asn Leu Lys Ile Glu Val Val Pro Asp Cys Gln Glu Lys Arg Ser Ser
465                 470                 475                 480

Gly Pro Ser Ser Ser Leu Asp Asn Gly Asn Ser Leu Asp Val Leu Lys
                485                 490                 495

Asn His Val Leu Asn Glu Leu Ile Gln Thr Glu Arg Val Tyr Val Arg
                500                 505                 510

Glu Leu Tyr Thr Val Leu Leu Gly Tyr Arg Ala Glu Met Asp Asn Pro
                515                 520                 525

Glu Met Phe Asp Leu Met Pro Pro Leu Leu Arg Asn Lys Lys Asp Ile
                530                 535                 540

Leu Phe Gly Asn Met Ala Glu Ile Tyr Glu Phe His Asn Asp Ile Phe
545                 550                 555                 560

Leu Ser Ser Leu Glu Asn Cys Ala His Ala Pro Glu Arg Val Gly Pro
                565                 570                 575

Cys Phe Leu Glu Arg Lys Asp Asp Phe Gln Met Tyr Ala Lys Tyr Cys
                580                 585                 590

Gln Asn Lys Pro Arg Ser Glu Thr Ile Trp Arg Lys Tyr Ser Glu Cys
                595                 600                 605

Ala Phe Phe Gln Glu Cys Gln Arg Lys Leu Lys His Arg Leu Arg Leu
                610                 615                 620

Asp Ser Tyr Leu Leu Lys Pro Val Gln Arg Ile Thr Lys Tyr Gln Leu
625                 630                 635                 640

Leu Leu Lys Glu Leu Leu Lys Tyr Ser Lys Asp Cys Glu Gly Ser Ala
                645                 650                 655

Leu Leu Lys Lys Ala Leu Asp Ala Met Leu Asp Leu Leu Lys Ser Val
                660                 665                 670

Asn Asp Ser Met His Gln Ile Ala Ile Asn Gly Tyr Ile Gly Asn Leu
                675                 680                 685

Asn Glu Leu Gly Lys Met Ile Met Gln Gly Gly Phe Ser Val Trp Ile
                690                 695                 700

Gly His Lys Lys Gly Ala Thr Lys Met Lys Asp Leu Ala Arg Phe Lys
705                 710                 715                 720

Pro Met Gln Arg His Leu Phe Leu Tyr Glu Lys Ala Ile Val Phe Cys
                725                 730                 735

Lys Arg Arg Val Glu Ser Gly Glu Gly Ser Asp Arg Tyr Pro Ser Tyr
                740                 745                 750
```

```
Ser Phe Lys His Cys Trp Lys Met Asp Glu Val Gly Ile Thr Glu Tyr
        755                 760                 765
Val Lys Gly Asp Asn Arg Lys Phe Glu Ile Trp Tyr Gly Glu Lys Glu
        770                 775                 780
Glu Val Tyr Ile Val Gln Ala Ser Asn Val Asp Val Lys Met Thr Trp
785                 790                 795                 800
Leu Lys Glu Ile Arg Asn Ile Leu Leu Lys Gln Gln Glu Leu Leu Thr
                805                 810                 815
Val Lys Lys Arg Lys Gln Gln Asp Gln Leu Thr Glu Arg Asp Lys Phe
            820                 825                 830
Gln Ile Ser Leu Gln Gln Asn Asp Glu Lys Gln Gln Gly Ala Phe Ile
        835                 840                 845
Ser Thr Glu Glu Thr Glu Leu Glu His Thr Ser Thr Val Val Glu Val
    850                 855                 860
Cys Glu Ala Ile Ala Ser Val Gln Ala Glu Ala Asn Thr Val Trp Thr
865                 870                 875                 880
Glu Ala Ser Gln Ser Ala Glu Ile Ser Glu Glu Pro Ala Glu Trp Ser
                885                 890                 895
Ser Asn Tyr Phe Tyr Pro Thr Tyr Asp Glu Asn Glu Glu Glu Asn Arg
            900                 905                 910
Pro Leu Met Arg Pro Val Ser Glu Met Ala Leu Leu Tyr
        915                 920                 925
```